(12) United States Patent
Herrmann et al.

(10) Patent No.: US 7,120,547 B2
(45) Date of Patent: Oct. 10, 2006

(54) PROCESS FOR CALIBRATION OF A MEDICAL-TECHNICAL DEVICE AND A MEDICAL-TECHNICAL DEVICE

(75) Inventors: Wolfgang Herrmann, Herzogenaurach (DE); Detlef Hofmann, Erlangen (DE); Stephan Welsing, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 384 days.

(21) Appl. No.: 10/246,655

(22) Filed: Sep. 19, 2002

(65) Prior Publication Data

US 2003/0097229 A1 May 22, 2003

(30) Foreign Application Priority Data

Sep. 19, 2001 (DE) ................ 101 46 210

(51) Int. Cl.
*G01D 18/00* (2006.01)

(52) U.S. Cl. ..................................... 702/85
(58) Field of Classification Search ............... 702/85, 702/8, 182–184; 707/104.1; 607/32; 340/568.1; 434/350; 235/375; 507/32; 700/90; 600/338, 600/407; 378/121
See application file for complete search history.

(56) References Cited

U.S. PATENT DOCUMENTS

| 5,994,770 A | 11/1999 | Harrington et al. |
| 6,036,661 A | 3/2000 | Schwarze et al. |
| 6,092,722 A * | 7/2000 | Heinrichs et al. ........... 235/375 |
| 6,356,780 B1 * | 3/2002 | Licato et al. ............... 600/407 |
| 6,394,353 B1 | 5/2002 | Schmitt |
| 6,412,980 B1 | 7/2002 | Lounsberry et al. |
| 6,535,714 B1 * | 3/2003 | Melker et al. .............. 434/350 |
| 6,574,518 B1 * | 6/2003 | Lounsberry et al. .......... 700/90 |
| 6,581,069 B1 * | 6/2003 | Robinson et al. ........ 707/104.1 |
| 2002/0040234 A1 * | 4/2002 | Linberg ....................... 607/32 |
| 2003/0025602 A1 * | 2/2003 | Medema et al. ......... 340/568.1 |

FOREIGN PATENT DOCUMENTS

JP         2001272410 A   * 10/2001

* cited by examiner

*Primary Examiner*—John Barlow
*Assistant Examiner*—Aditya Bhat
(74) *Attorney, Agent, or Firm*—Young & Thompson

(57) ABSTRACT

The invention relates to a process for calibration of a medical-technical device which is in operation as a result of mounting a new component on the medical-technical device. The invention moreover relates to a medical-technical device which is made such that it automatically identifies the new component when a new component is mounted on the medical-technical device and displays the necessary steps for calibration of the medical-technical device based on the identification. The medical-technical device however can also be made such that it automatically identifies the newly attached component after its identification.

28 Claims, 3 Drawing Sheets

PROCESS FOR CALIBRATION OF A MEDICAL-TECHNICAL DEVICE AND A MEDICAL-TECHNICAL DEVICE

FIELD OF THE INVENTION

The invention relates to a process for calibration of a medical-technical device which is in operation as a result of mounting a new component on the medical-technical device. The invention moreover relates to a medical-technical device which is made such that it automatically identifies the new component when the latter is mounted on the medical-technical device.

BACKGROUND OF THE INVENTION

If in a medical-technical device which is in operation a replacement part or an additional component is installed or connected, a service technician who is installing or connecting the replacement part or the additional component must generally recalibrate the medical-technical device. The concept of "calibration" is understood in its widest sense in connection with this application. Calibration is defined among others as the adjustment of the medical-technical device including the new component, or when the new component is for example a software update, configuration of the computer which comprises the medical-technical device. The service technician during calibration can consult suitable manuals which include instructions for calibration of the medical-technical device.

Based on legal regulations the manufacturer of the medical-technical device when the replacement part or additional component is installed must keep a record of the installed replacement part or the installed additional component and about the corresponding medical-technical device. Therefore the service technician after completion of the installation notates the identification number assigned to the installed replacement part or the installed additional component, for example a material number, a serial number, or an inspection number of the replacement part or the additional component, and communicates this to the central administrative department of the manufacturer. In the administrative department these identification numbers are entered in a suitable database or card file.

SUMMARY OF THE INVENTION

The object of the invention is therefore to devise a process and a medical-technical device such that there is the prerequisite for easier calibration of the medical-technical device on which the new component is located.

The first object of the invention is achieved by a process for calibration of a medical-technical device which is in operation as a result of the attachment of a new component to the medical-technical device, having the following process steps:

automatic identification of the new component by the medical-technical device and based on the identification of the new component, display of the steps necessary for calibration of the medical-technical device by the latter.

The first object of the invention is also achieved by a process for calibration of a medical-technical device which is in operation as a result of mounting a new component on the medical-technical device, having the following process steps:

automatic identification of the new component by the medical-technical device andbased on the identification of the new component, automatic calibration of the medical-technical device.

Therefore a new component is mounted on the medical-technical device which is in operation, therefore which has already been installed and is being used properly. The new component replaces, for example, according to versions of the invention, a component of the medical-technical device or is mounted additionally on the medical-technical device. The new component is thus especially a replacement part or retrofit of the medical-technical device. As a result of the mounting of the new component on the medical-technical device, which can be for example installation or connection of the new component or reading in new software into the computer which has the medical-technical device, the medical-technical device must generally be recalibrated. The concept "calibration of the medical-technical device" should otherwise be understood in the widest sense. It comprises especially necessary adjustments on the medical-technical device or the newly mounted component and also configuration of the computer so that the medical-technical device is ready again for operation in the proper manner with the newly mounted component.

As claimed in the invention the medical-technical device automatically identifies the new component which has been newly mounted on the medical-technical device. Then, the medical-technical device for example with a monitor of the medical-technical device displays the individual steps which are necessary for the calibration of the medical-technical device and which then are carried out by the service technician who has mounted the new component on the medical-technical device. Thus the service technician does not need to consult the manual for calibration. But all necessary steps for calibration of the medical-technical device are displayed to him. Therefore he is guided by the medical-technical device through the individual steps of calibration which are to be carried out.

Instead of displayed steps, the medical-technical device can also be automatically calibrated. Based on the identification of the new component, for example a computer program stored in the computer of the medical-technical device can be automatically retrieved, which thereupon automatically executes the steps necessary for calibration of the medical-technical device. These steps can be among others automatically taken measurements. Consequently the service technician must simply mount the new component on the medical-technical device. The necessary measures for calibration of the medical-technical device are then either carried out automatically or the steps which the service technician is to carry out are displayed. Thus the medical-technical device can be quickly, reliably and easily transferred again into a serviceable state as a result of installation of an additional component or based on replacement of a component. Calibration is consequently facilitated, by which expensive work time can be saved.

According to one especially preferred embodiment of the invention, it is provided that the new component has a part which comprises a data record suitable for identification of the new component. This data record according to versions of the invention comprises a serial number, an inspection number and/or a material number and/or at least one important characteristic of the new component. This data record is read out according to one especially preferred version of the invention by the computer of the medical-technical device so that the medical-technical device identifies the new component. A part which is suitable for the purposes of the process as claimed in the invention is described for example in U.S. Pat. No. 5,994,770, reference to the disclosure contents of which is hereby made. The part of U.S. Pat. No. 5,994,770 is a part for storage of data for identifying products. This part can be read out electronically.

According to another version of the invention, it is provided that after identification of the new component the medical-technical device sends a message to a central data processing system, the message comprising an entry about the medical-technical device and the new component. As stated in the introduction, manufacturers of medical-technical devices are legally mandated to keep a record of installed or supplied components of the medical-technical device. As claimed in the invention therefore the medical-technical device, after it has identified the new component, generates the message and sends it to the central data processing system. The central data processing system can be located for example in the headquarters of the manufacturer. Based on the message sent to the central data processing system it is possible for the manufacturer to easily acquire delivered and/or installed components of medical-technical devices and to keep the legally mandated record. The manufacturer is thus able to easily keep information about the location of components of medical-technical devices manufactured, installed or delivered by him.

According to one embodiment of the invention, the message comprises an entry about the serial number, material number and/or an inspection number of the new component.

If according to one especially preferred embodiment of the invention the message is generated after calibration of the medical-technical device and is sent to the central data processing system and if it comprises the data generated during calibration, proper installation of the new component can be easily monitored and recorded.

According to one version of the invention the message is transmitted via a long-distance data transmission means, as for example the telephone network or the Internet, to the central data processing system.

According to one version, the medical-technical device is a magnetic resonance device, a computer tomograph, an x-ray device, a lithotripter, an ultrasonic device, an isotope scanner or a device for radiation therapy. An isotope scanner is used otherwise especially in nuclear medicine.

The second object of the invention is achieved by a medical-technical device which is made such that it automatically identifies the new component when the latter is mounted on the medical-technical device and displays the necessary steps for calibration of the medical-technical device based on the identification.

The second object of the invention is likewise achieved by a medical-technical device which is made such that it automatically identifies the new component when the latter is mounted on the medical-technical device and automatically carries out calibration based on the identification.

Mounting of a new component which according to embodiments of the invention replaces a component of the medical-technical device or is mounted additionally on the medical-technical device, is for example the installation or connection of the new component. Mounting can also be however copying of a software update onto a computer which comprises the medical-technical device. After mounting the new component, the medical-technical device as claimed in the invention automatically recognizes the new component and thereupon for example on a display of the medical-technical device displays the necessary steps for calibration of the medical-technical device. The calibration steps can then be carried out by the service technician.

Alternatively the medical-technical device, after it has identified the new component, can be automatically calibrated. Calibration in this connection means especially resetting the medical-technical device with the newly mounted component, which resetting is necessary due to the mounting of the new component. If it is a software update, calibration of the medical-technical device in particular is reconfiguration of the computer of the medical-technical device which may have become necessary.

Advantageous embodiments of the invention result from the dependent claims. Thus, according to one embodiment of the invention, among others it is provided that the new component has a part which comprises a data record which is suitable for identification of the new component. In this component, as is described for example in U.S. Pat. No. 5,994,770, according to one embodiment of the invention a serial number, an inspection number and/or a material number of the new component can be stored. The data record of the part can also comprise an entry about at least one important characteristic of the new component, according to another version of the invention.

Consequently it is possible for the medical-technical device to identify the new component by its reading out the data record of the part of the new component with the computer of the medical-technical device, as is provided especially according to one version of the invention.

As already described in the introduction, manufacturers of medical-technical devices are obligated to keep a record of installed replacement parts and new components. In one especially advantageous embodiment of the invention it is therefore provided that the medical-technical device after identification of the new component generates a message and sends it to a central data processing system, the message comprising an entry about the medical-technical device and the new component. In the central data processing system, based on the message for example it is easily possible to store in a database where and in which medical-technical device the new component, for example, the replacement part or the newly mounted component, is installed. Manual detection of the newly mounted part is thus eliminated, by which reliable detection of the newly arranged component is greatly simplified.

The message can comprise especially according to one version of the invention an entry about a serial number, a material number and/or an inspection number of the new component.

If according to one especially preferred version of the invention, during calibration the data assigned to calibration are generated and these data are transmitted at least as part of the message to the central data processing system after completion of calibration, in the central data processing system a record can be additionally kept about the correct arrangement of the new component. Moreover, it is easily possible to centrally monitor whether the medical-technical device has been properly calibrated.

According to another version of the invention, the message is sent via a long-distance data transmission means to the central data processing system. The long-distance data transmission means is for example the Internet, ISDN (Integrated Services Digital Network) or a suitable telephone network.

According to another version of the invention the medical-technical device is a magnetic resonance device, a computer tomograph, an x-ray device, an lithotripter, an ultrasonic device, an isotope scanner or a device for radiation therapy. If for example the medical-technical device as claimed in the invention is a magnetic resonance device and a customer as an option buys an additional head coil for the magnetic resonance device, the head coil is delivered to the customer and then installed in the magnetic resonance device by the service technician. After installing the head coil the magnetic resonance device automatically recognizes the serial number, the inspection number and the material number of the head coil and acquires them. Then the magnetic resonance device automatically initiates the corresponding electrical calibration and in doing so prepares calibration tables, for example. In the course of this electrical calibration, individual steps to be carried out by the service technician can be displayed on the display of the magnetic resonance device. The electrical calibration can however also be carried out independently by the magnetic resonance device. Within a very short time the customer can use the new head coil. Moreover, the data electronically acquired by the magnetic resonance device can be remotely transmitted to the headquarters of the manufacturer of the magnetic resonance device. In the main headquarters is the central data processing system in which the electronically acquired data are stored in a special database. With the data stored in the database thus a record of the delivered and installed option, i.e. the aforementioned head coil, is easily possible.

BRIEF DESCRIPTION OF THE DRAWINGS

One embodiment of the invention is shown by way of example in the schematics.

DETAILED DESCRIPTION OF THE INVENTION

Figure 1:
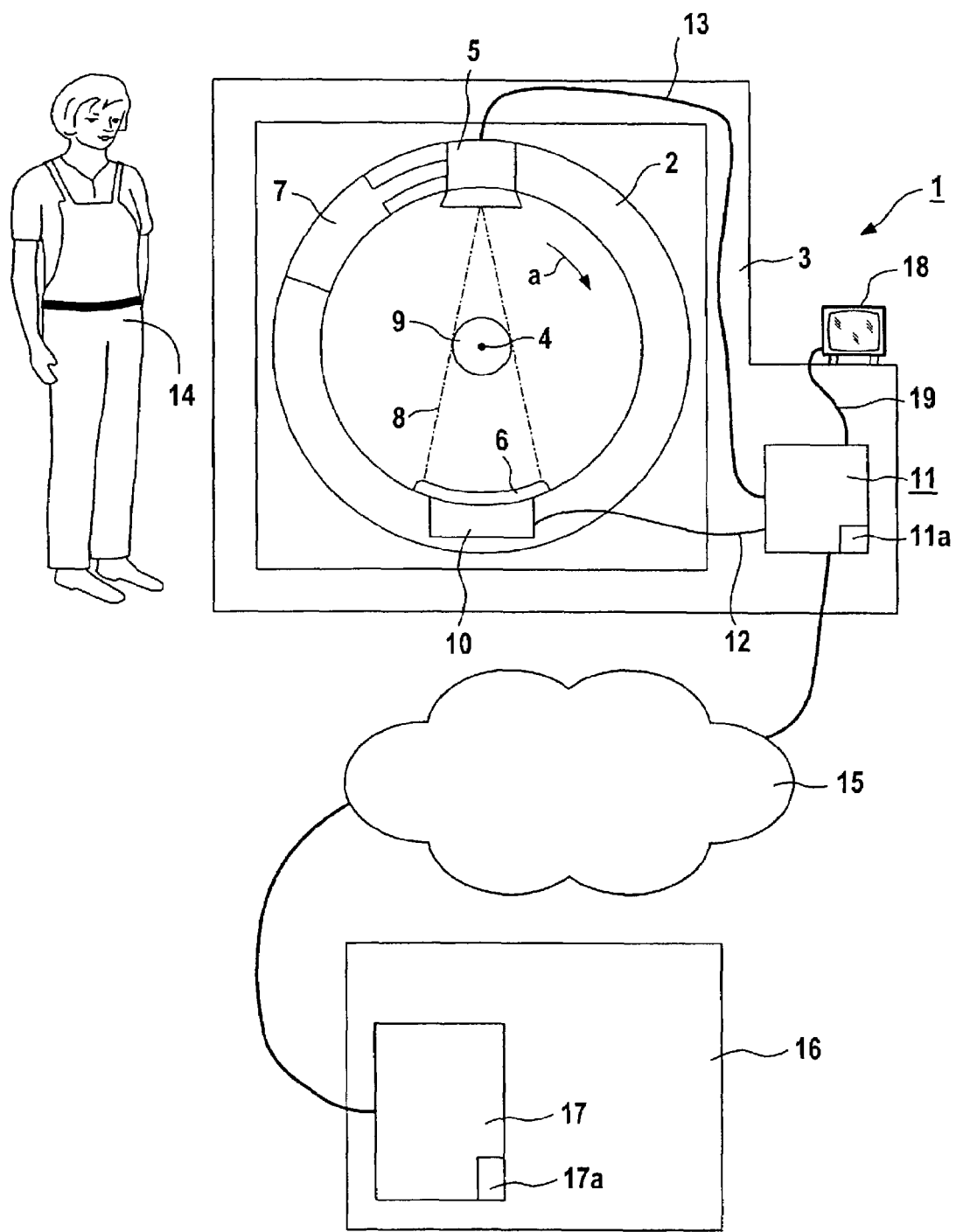
FIG. 1 shows a computer tomograph.

FIG. 1 shows by way of example and schematically a side view of a computer tomograph 1 with an annularly made gantry 2 which is supported on the stationary housing 3 of the computer tomograph 1 to be able to turn in the direction of the arrow a around an axis of rotation 4 aligned at a right angle to the axis of the paper of FIG. 1. The housing 3 of the computer tomograph 1 in the case of this embodiment is not detailed.

On the gantry 2 there are several components which in the case of this embodiment comprise an x-ray source 5, a radiation detector 6 opposite the x-ray source 5, and a cooling means 7 which is not detailed for dissipating the heat which is produced by the x-ray tube of the x-ray source 5 in operation of the computer tomograph 1. In operation of the computer tomograph 1 the gantry 2 rotates around the axis 4 of rotation, a fan-shaped x-ray beam emerging from the x-ray source 5 penetrating the measurement field 9 at different projection angles and striking the radiation detector 6. From the output signals of the radiation detector 6 which arise a data acquisition device 10 forms the measured values which are sent to the control computer 11 of the computer tomograph 1. The control computer 11 computes therefrom a picture of the patient who is in the measurement field 9 and who is not shown in FIG. 1. In the case of this embodiment the data acquisition device 10 is connected to the control computer 11 with an electrical line 12 which contains for example a slip ring system or a wireless transmission section in a manner which is not shown. The electrical connections of the x-ray source 5 and of the radiation detector 6 are accomplished in a conventional manner which is not shown. The picture computed by the control computer 11 can then be viewed with the monitor 18 which is connected to the control computer 11 with an electrical line 19.

Figure 2:
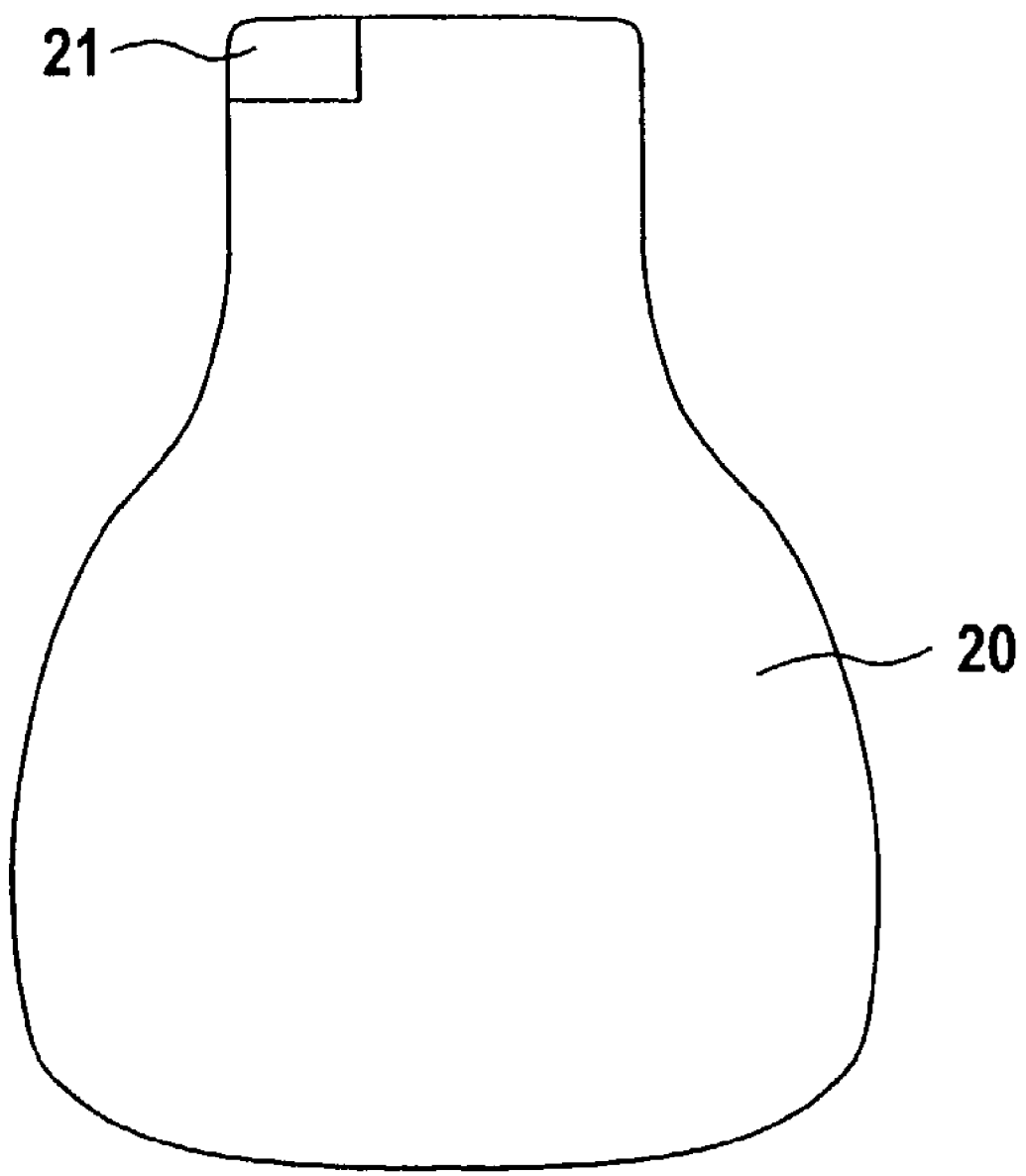
FIG. 2 shows an x-ray tube and
FIG. 3 shows a flowchart.
Figure 3:
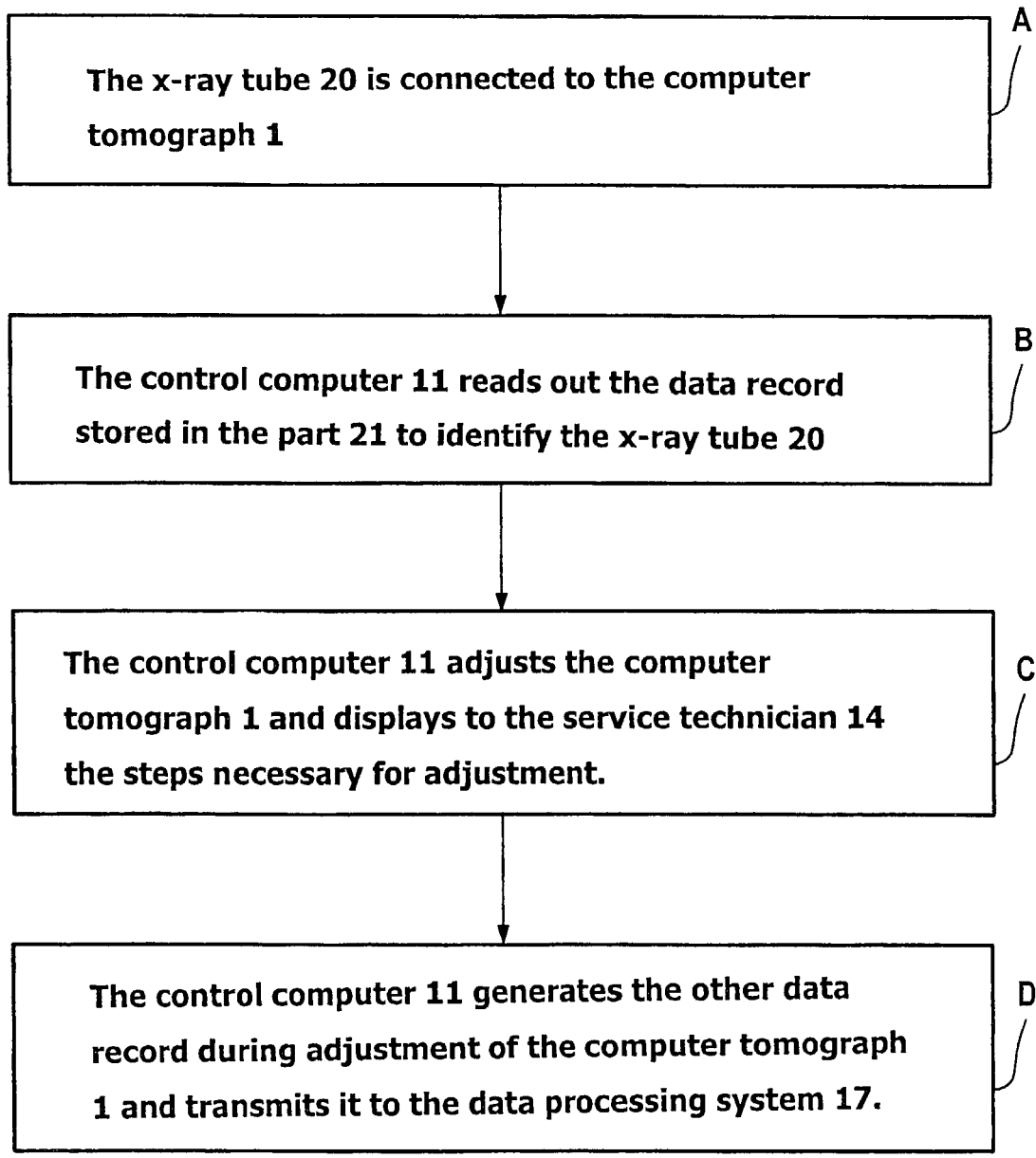

In the case of this embodiment, the x-ray tube of the x-ray device 5 is defective. It was therefore replaced by a service technician 14 with the x-ray tube 20 shown in FIG. 2. The x-ray tube 20 in the case of this embodiment comprises an electronic part 21 which is mounted on the x-ray tube 20. The part 21 stores a data record which in the case of this embodiment comprises the serial, material and inspection numbers of the x-ray tube 20. An electrical voltage necessary for operation of the part 21 takes place via an electrical line 13 which in a manner not shown comprises a slip ring system and with which the part 21 after installation of the x-ray tube 20 in the computer tomograph 1 is connected to the control computer 11 of the computer tomograph. One embodiment of the component 21 is otherwise described in U.S. Pat. No. 5,994,770, the disclosure contents of which are hereby included (step A of the flow chart shown in FIG. 3).

In the case of this embodiment, data are also transmitted from the part 21 via the electrical line 13 to the control computer 11 so that after connection of the x-ray tube 20 a computer program stored in the control computer 11 reads out the data record stored in the part 21. As a result of reading out of the data record the computer program stored in the control computer 11 automatically identifies the newly mounted x-ray tube 20 (step B of the flow chart shown in FIG. 3).

Based on the identification of the newly mounted x-ray tube 20 on the computer tomograph 1 the computer program stored in the control computer 1 begins to automatically reset the computer tomograph 1 with the newly connected x-ray tube 20. During the automatic adjustment it is necessary among others for the service technician 14 to carry out individual steps for making the adjustments. The computer program stored in the control computer 11 is therefore executed such that it displays these necessary steps to the service technician 14 on the monitor 18. One example of this step is triggering of the x-radiation of the x-ray tube for test purposes (step C of the flow chart shown in FIG. 3).

During adjustment of the computer tomograph 1, the computer program stored in the control computer 11 generates another data record that checks whether the computer tomograph 1 has been properly set so that it can be used properly again. The further data record likewise comprises an entry about the serial number, the material number, and the inspection number of the x-ray tube 20 and an entry for identification of the computer tomograph 1. This data record is stored in the case of this embodiment in a database 11a of the control computer 11.

In the case of this embodiment, the control computer 11 of the computer tomograph 1 is moreover connected to the public telephone network 15 so that it can transmit data to the data processing system 17 which is likewise connected to the public telephone network 15. The data processing system 17 is located in the case of this embodiment in an office 16 of the manufacturer of the computer tomograph 1.

After the computer tomograph 1 has been adjusted, the control computer 11 automatically transmits the other data record generated during adjustment of the computer tomograph 1 to the data processing system 17. The data processing system 17 furthermore comprises a database 17a in which this other data record is stored. Since the other data record comprises information suitable for identification of the x-ray tube 20 and for identification of the computer tomograph 1, it can be used for the legally mandated record of the location of the installed x-ray tube 20 (step D of the flow chart shown in FIG. 3).

In the case of this embodiment the installation of a replacement part in the form of the x-ray tube 20 in the computer tomograph 1 is described. Other components of the computer tomograph 1, such as for example the gantry 2, the radiation detector 6, the cooling means 7, the data acquisition device 10, the control computer 11, etc. can likewise be replaced by a suitable replacement part.

But it is also possible for the additional component, for example a laser light sight, to be connected to the computer tomograph 1. Here a new component can also be a software update and the adjustment of the computer tomograph 1 can be reconfiguration of the control computer 11 which is necessary because of a software update.

The process as claimed in the invention can also be used for another medical-technical device, such as for example for a magnetic resonance device, a lithotripter, an ultrasonic device, an x-ray device, an isotope scanner or a device for radiation therapy. A medical-technical device as claimed in the invention need not necessarily be a computer tomograph.

The described embodiment is otherwise only of an exemplary nature.

The invention claimed is:

1. Process for calibration of a medical-technical device which is in operation as a result of the attachment of a new component to the medical-technical device, which comprises the following process steps:
   automatically identifying the new component by the medical-technical device;
   based on the identification of the new component, automatically retrieving steps necessary for calibration of the medical-technical device from at least one of the medical technical-device and the new component and automatically calibrating the medical-technical device by carrying out the retrieved steps; and
   after identifying the new component, the medical-technical device generates a message and sends it to the central data processing system, the message comprising an entry about the medical-technical device and the new component.

2. Process as claimed in claim 1, in which the new component replaces a component of the medical-technical device.

3. Process as claimed in claim 1, in which the new component is a component which can be attached additionally to the medical-technical device.

4. Process as claimed in claim 1, in which the new component has a part which comprises a data record which is suitable for identification of the new component.

5. Process as claimed in claim 4, in which the data record comprises a serial number, an inspection number and/or a material number of the new component.

6. Process as claimed in claim 4, in which the data record comprises at least one important characteristic of the new component.

7. Process as claimed in claim 4, in which the medical-technical device identifies the new component by its reading out the data record of the part of the new component with the computer of the medical-technical device.

8. Process as claimed in claim 1, in which the message comprises an entry about the serial number, the material number and/or the inspection number of the new component.

9. Process as claimed in claim 1, in which the message is generated after calibration of the medical-technical device and is sent to the central data processing system and it comprises the data generated during calibration.

10. Process as claimed in claim 1, in which the message is transmitted via a long-distance data transmission means to the central data processing system.

11. Process as claimed in claim 1, in which the medical-technical device is a magnetic resonance device, a computer tomograph, an x-ray device, a lithotripter, an ultrasonic device, an isotope scanner or a device for radiation therapy.

12. Process for calibration of a medical-technical device which is in operation as a result of the attachment of a new component to the medical-technical device, which comprises the following process steps:
   automatically identifying the new component by the medical-technical device;
   calibrating the medical-technical device based on the identification of the new component;
   after identifying the new component, the medical-technical device generating a message and sending the message to a central data processing system, the message comprising an entry about the medical-technical device and the new component; and
   wherein the message is generated after calibration of the medical-technical device and is sent to the central data processing system and it comprises the data generated during calibration.

13. Process as claimed in claim 12, in which the message comprises an entry about the serial number, the material number and/or the inspection number of the new component.

14. Process for calibration of a medical-technical device which is in operation as a result of the attachment of a new component to the medical-technical device, which comprises the following process steps:
   automatically identifying the new component by the medical-technical device;
   calibrating the medical-technical device based on the identification of the new component;
   after identifying the new component, the medical-technical device generating a message and sending the message to a central data processing system, the message comprising an entry about the medical-technical device and the new component; and
   transmitting the message via a long-distance data transmission means to the central data processing system.

15. Medical-technical device comprising:
   means for automatically identifying a new component when the new component is mounted on the medical-technical device;
   means for automatically retrieving steps necessary for calibration of the medical-technical device from at least one of the medical technical-device and the new component and automatically calibrating the medical-technical device based on the identification by carrying out the retrieved steps; and
   the medical technical device is made such that after identifying the new component the medical-technical device generates a message and sends it to the central data processing system, the message comprising an entry about the medical-technical device and the new component.

16. Medical-technical device as claimed in claim 15, in which the new component replaces the component of the medical-technical device.

17. Medical-technical device as claimed in claim 15, in which the new component is a component to be mounted additionally on the medical-technical device.

18. Medical-technical device as claimed in claim 15, in which the new component has a part which comprises a data record which is suitable for identification of the new component.

19. Medical-technical device as claimed in claim 18, in which the data record comprises an entry about the serial number, the inspection number and/or the material number of the new component.

20. Medical-technical device as claimed in claim 18, in which the data record comprises an entry about at least one important characteristic of the new component.

21. Medical-technical device as claimed in claim 18, in which the medical-technical device identifies the new component by its reading out the data record of the part of the new component with the computer of the medical-technical device.

22. Medical-technical device as claimed in claim 15, in which the message comprises an entry about the serial number, the material number and/or the inspection number of the new component.

23. Medical-technical device as claimed in claim 15, in which the message is generated after calibration of the medical-technical device and is sent to the central data processing system and it comprises the data generated during calibration.

24. Medical-technical device as claimed in claim 15, in which the message is transmitted via a long-distance data transmission means to the central data processing system.

25. Medical-technical device as claimed in claim 15, which is a magnetic resonance device, a computer tomograph, an x-ray device, a lithotripter, an ultrasonic device, an isotope scanner or a device for radiation therapy.

26. Medical-technical device comprising:
   means for automatically identifying a new component when the new component is mounted on the medical-technical device; and
   means for calibrating the medical-technical device based on the identification,
   in which the medical technical device is made such that after identifying the new component the medical-technical device generates a message and sends it to a central data processing system, the message comprising an entry about the medical-technical device and the new component, and in which the message is generated after calibration of the medical-technical device and is sent to the central data processing system and it comprises the data generated during calibration.

27. Medical-technical device as claimed in claim 26, in which the message comprises an entry about the serial number, the material number and/or the inspection number of the new component.

28. Medical-technical device comprising:
   means for automatically identifying a new component when the new component is mounted on the medical-technical device; and
   means for calibrating the medical-technical device based on the identification,
   in which the medical technical device is made such that after identifying the new component the medical-technical device generates a message and sends it to a central data processing system, the massage comprising an entry about the medical-technical device and the new component, and in which the message is transmitted via a long-distance data transmission means to the central data processing system.

* * * * *